US011185513B1

(12) United States Patent
El-Say et al.

(10) Patent No.: US 11,185,513 B1
(45) Date of Patent: Nov. 30, 2021

(54) TRANSFERSOME-CONTAINING TRANSDERMAL FILM FORMULATIONS AND METHODS OF USE

(71) Applicant: King Abdulaziz University, Jeddah (SA)

(72) Inventors: Khalid M. El-Say, Jeddah (SA); Omar D. Al-hejaili, Jeddah (SA); Abdullah A. Alamoudi, Jeddah (SA); Osama A. A. Ahmed, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/314,128

(22) Filed: May 7, 2021

(51) Int. Cl.
*A61K 9/70* (2006.01)
*A61K 47/10* (2017.01)
*A61K 47/24* (2006.01)
*A61K 31/506* (2006.01)

(52) U.S. Cl.
CPC .......... *A61K 9/7069* (2013.01); *A61K 31/506* (2013.01); *A61K 47/10* (2013.01); *A61K 47/24* (2013.01)

(58) Field of Classification Search
None
See application file for complete search history.

(56) References Cited

U.S. PATENT DOCUMENTS 10,751,294 B1 * 8/2020 Ahmed .................... A61K 9/10
2011/0142956 A1 6/2011 Peuker
2013/0053393 A1 * 2/2013 Frangakis ................. A61P 1/04 514/252.16
2018/0243224 A1 * 8/2018 Banait .................. A61K 9/4858

OTHER PUBLICATIONS

Hawkinswatts ([retrieved from on-line website: https://www.hawkinswatts.com/wp-content/uploads/2016/01/Hawkins-Watts-HLB-Balance.pdf], last visit Jul. 2, 2021]) (Year: 2016).*
Ahmed et al., "Optimized vinpocetine-loaded vitamin E D-α-tocopherol polyethylene glycol 1000 succinate-alpha lipoic acid micelles as a potential transdermal drug delivery system: in vitro and ex vivo studies", International Journal of Nanomedicine 2019:14 33-43.
Badr-Eldin et al., "Optimized nano-transfersomal films for enhanced sildenafil citrate transdermal delivery: ex vivo and in vivo evaluation", Drug Design, Development and Therapy 2016:10 1323-1333.
Nangare et al., "Smart invasome synthesis, characterizations, pharmaceutical applications, and pharmacokinetic perspective: a review", Future Journal of Pharmaceutical Sciences (2020) 6:123.
Opatha et al., "Transfersomes: A Promising Nanoencapsulation Technique for Transdermal Drug Delivery", Pharmaceutics (2020) 12:855.

* cited by examiner

*Primary Examiner* — Kyung S Chang
(74) *Attorney, Agent, or Firm* — W&C IP

(57) ABSTRACT

A transdermal film formulation containing transfersomes incorporated onto the transdermal film is provided. The transfersomes include avanafil, a phospholipid, and an edge activator, wherein the phospholipid to avanafil ratio is from 3.5:1 to 4.5:1 and wherein the edge activator has a hydrophilic-lipophilic (HLB) value of 2-4. Methods of making the transdermal film formulation and methods of delivering avanafil using the transdermal film formulation are also provided.

12 Claims, 7 Drawing Sheets

TRANSFERSOME-CONTAINING TRANSDERMAL FILM FORMULATIONS AND METHODS OF USE

FIELD OF THE INVENTION

The invention is generally related to transdermal films loaded with transfersomes encapsulating an active agent and methods of use thereof.

BACKGROUND OF THE INVENTION

Erectile dysfunction (ED) is the most common sexual complaint submitted by men to their health care providers [1]. It is not commonly seen as a life-threatening illness, but it is closely linked to several important physical conditions and it can impact psychosocial wellbeing. Therefore, ED has a significant influence on patients' quality of life [2]. In Arab countries, recent studies show that the prevalence of ED is more than 40% and is linked to a variety of risk factors such as age, obesity, lack of activity, smoking, and diabetes mellitus complications [3,4]. The main goals of ED management are to monitor and minimize risk factors associated with organic cardiovascular and to regain the ability to get an efficient penile erection and sustain it [5]. The disease's etiology must be determined and treated where possible and not only to treat symptoms [6].

Phosphodiesterase type 5 inhibitors (PDE5-Is) are orally active and self-administered drugs for the treatment of ED that are used as needed before sexual intercourse [7]. Avanafil (AVA) (Stendra®) is a second-generation and highly selective PDE5-I for ED treatment [8]. In 2012, it was approved by the United States of Food and Drug Administration (US-FDA) and in the following year, it was approved by The European Medicines Agency (EMA) [9]. AVA is subject to significant first-pass metabolism through the human cytochrome P450 enzyme system [7]. According to the BCS, it is classified as a Class II drug, thus its dissolution is the rate-limiting step for its absorption that leads to poor oral bioavailability. Also, AVA absorption is altered in the presence of food which delays the time required to reach its maximum serum concentration [8].

Lipid-based drug delivery systems are a potential controlled approach to deliver drugs with various molecular weights. Furthermore, these delivery systems can improve the solubility of a poorly soluble drug and thus improve its bioavailability [10]. In 1992, a novel lipid-based vesicle known as transfersomes (TRF) that is composed of phospholipid and edge activator was introduced [11,12]. Because of the presence of the edge activator which often is a single chain surfactant with a high radius of curvature, they are highly deformable vesicles commonly used for non-invasive delivery of drugs [13]. By squeezing themselves along the intracellular sealing lipid, TRF can easily penetrate the pores of the subcutaneous layer (SC) [14,15]. When TRF is applied under non-occlusive conditions, it follows the natural water gradient across the epidermis due to the flexibility of the membrane that reduces the risk of vesicle rupture in the skin [13,16].

Due to the bioavailability problems with oral delivery of AVA, alternative and effective formulations for AVA delivery are needed.

SUMMARY OF THE INVENTION

The disclosure provides AVA loaded in ultra-deformable nanovesicles to improve the AVA permeability through the skin. The AVA-loaded transfersomes are incorporated in transdermal films to mitigate the food effect and avoid the first-pass metabolism, thus providing a transdermal delivery system with enhanced efficacy and bioavailability.

An aspect of the disclosure provides a transdermal film formulation, comprising transfersomes incorporated onto the transdermal film, wherein the transfersomes comprise avanafil, a phospholipid, and an edge activator, wherein the phospholipid to avanafil ratio is from 3.5:1 to 4.5:1 and wherein the edge activator has a hydrophilic-lipophilic (HLB) value of 2-4. In some embodiments, the phospholipid is phosphatidylcholine stabilized with ascorbyl palmitate. In some embodiments, the phospholipid to edge activator ratio is from 2.5:1 to 3.5:1. In some embodiments, the film further comprises hydroxypropyl methylcellulose (HPMC), citral, and propylene glycol. In some embodiments, the HPMC is present in an amount of 1-5% w/v. In some embodiments, the citral is present in an amount of 1-5% w/v. In some embodiments, the propylene glycol is present in an amount of 1-5% w/v.

Another aspect of the disclosure provides a method of making a formulation as described herein, comprising preparing transfersomes comprising avanafil, a phospholipid, and an edge activator, wherein the phospholipid to avanafil ratio is from 3.5:1 to 4.5:1, wherein the edge activator has a hydrophilic-lipophilic (HLB) value of 2-4, and wherein the transfersomes are present in a hydration medium at a pH of 7.5-8.5; mixing the transfersomes with a film-forming polymer, a penetration enhancer, and a plasticizer to produce a gel; and drying the gel to produce a film. In some embodiments, the film-forming polymer is HPMC, the penetration enhancer is citral, and the plasticizer is propylene glycol.

Another aspect of the disclosure provides a method of delivering avanafil to a subject in need thereof, comprising applying a transdermal film formulation as described herein to a skin surface of the subject.

DETAILED DESCRIPTION

Figure 1A:
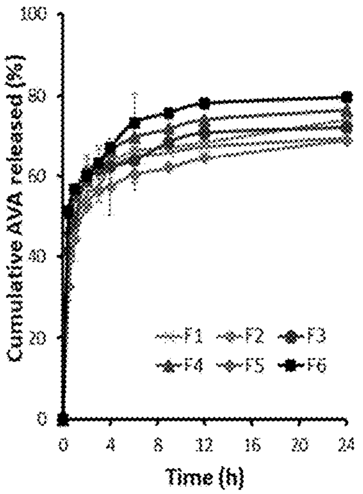
FIGS. 1A-C. Release profile of Draper-Lin small composite design formulations a) for F1-F6; b) for F7-F12; and c) for F13-F18.

Embodiments of the disclosure provide transdermal film formulations having enhanced bioavailability of a drug which is loaded in transfersomes.

Transfersomes are flexible forms of liposomes made from a combination of a lipid (for example, soy phosphatidylcholine) and an edge activator (for example, a fatty acid or surfactant) that can pass through the skin surface. These vesicular carrier systems have at least one inner aqueous compartment that is enclosed by a lipid bilayer, together with an edge activator/surfactant. These vesicles may be used as vehicles for transporting active agents into the body via the transdermal route, either by placing the active agent to be transported inside the lumen of the vesicle or incorporating the active agent into the membrane of the vesicle, as one of the membrane components.

Phospholipids that may be incorporated in the transfersome include, but are not limited to, phosphatidylcholine stabilized with ascorbyl palmitate (i.e. Phospholipon 90 G), soy or egg phosphatidylcholine, dipalmitoylphosphatidylcholine, and dilauroyl L-α-phosphatidylcholine. In some embodiments, the formulation includes 500-800 mg phospholipids, e.g. 600-700 mg, e.g. about 682 mg.

Edge activators function as membrane-destabilizing factors to increase the deformability of vesicle membranes and, when combined in a proper ratio with an appropriate lipid, gives the optimal mixture, enabling the transfersomes to become deformable, as well as ultra-flexible, which results in a higher permeation capability. Edge activators are amphiphilic molecules that contain a lipophilic alkyl chain that is connected to a hydrophilic head group. Generally, rather than cationic surfactants, anionic surfactants are furthermore effective in enhancing the skin penetration, and the critical micelle concentration is also lower, whereas nonionic surfactants with an uncharged polar head group are better-tolerated than cationic and anionic surfactants. Nonionic surfactants are considered less toxic and less hemolytic, as well as less irritating to cellular surfaces, and they tend to maintain a near physiological pH in a solution. Suitable surfactants that may be utilized as an edge activator include, but are not limited to, sodium cholates; sodium deoxycholate; Tweens and Spans (e.g. Tween 20, Tween 60, Tween 80, Span 60, Span 65 and Span 80) and dipotassium glycyrrhizinate. In some embodiments, the formulation includes 20-200 mg surfactant, e.g. 30-50 mg or about 170-190 mg. In some embodiments, the formulation contains a mixture of two or more surfactants. In some embodiments, the formulation contains Span 80 and Span 85. In some embodiments, the formulation contains about 182 mg of Span 80 and about 45.5 mg of Span 85.

The hydrophilic-lipophilic balance (HLB) of a surfactant is measured on an empirical scale developed by Griffin (W. C. Griffin, J. Cosmet. Chem., 1, 311, 1949). This scale ranges from 0 to 20, with 0 for a completely lipophilic molecule and 20 for a completely hydrophilic molecule. In some embodiments, the surfactant has a HLB value of about 1-5, e.g. about 2-4.

The transfersomes described herein are useful for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is a PDE-5 inhibitor, such as avanafil, sildenafil, vardenafil, tadalafil, udenafil, microdenafil, lodenafil carbonate, active components of Epimedium extracts, and other natural and synthetic analogues as described e.g. in Patel et al., Screening of synthetic PDE-5 inhibitors and their analogues as adulterants: Analytical techniques and challenges, J. Pharm. Biomed. Anal. 87 (2014) 176-190, herein incorporated by reference; and in US patent application 20150231092, the complete contents of which is hereby incorporated by reference. In some embodiments, the amount of active agent incorporated into the composition is 50-150 mg, e.g. 75-125 mg, e.g. about 100 mg. In some embodiments, the phospholipid to active agent ratio is from 3:1 to 5:1, e.g. 3.5:1 to 4.5:1, e.g. about 4:1.

The transfersomes described herein are further incorporated onto transdermal films. A transdermal film, which may be incorporated into a patch, is a medicated film that is placed on the skin to deliver a specific dose of medication through the skin and into the bloodstream. An advantage of a transdermal drug delivery route over other types of medication delivery such as oral, topical, intravenous, intramuscular, etc. is that the film provides a controlled release of the medication into the patient, usually through either a porous membrane covering a reservoir of medication or through body heat melting thin layers of medication embedded in the adhesive. Typical components of a patch include a liner which protects the patch during storage and is removed prior to use, drug, adhesive, membrane, backing, permeation enhancers, stabilizers, preservatives, etc. In some embodiments, the film has a thickness of 0.25-0.45 mm, e.g. about 0.35 mm.

In some embodiments, the film forming polymers incorporated in the transdermal film as described herein are selected from hydroxypropyl methylcellulose (HPMC), hydroxypropyl cellulose, polyvinyl pyrrolidone, vinylpyrrolidone-vinyl ace-tate copolymer 40:60, ethylcellulose, acrylic-acid ester copolymers and methacrylic acid ester copolymers with trimethylammonium methyl acrylate, copolymers of dimethylaminomethacrylic acid and neutral methacrylic acid esters, shellac, cellulose acetate phtha-late, hydroxypropyl methylcellulose phthalate, polymers of meth-acrylic acid and methacrylic acid esters, ethyl acrylate-methacrylic acid methyl ester copolymer 70:30, methacrylic acid-methyl acry-late copolymer 50:50, gelatin, polyvinyl acetate, methacrylate, acrylate dispersions, polyether-polyamide block copolymer, poly-ethylene-methyl-methacrylate block copolymer, polyurethanes, polyester block copolymer, polyisobutylene-styrene-styrene co-8 polymers, styrene-butadiene-styrene-isoprene copolymers, ethyl-ene-vinyl acetate copolymers, polyamide, nitrocellulose, as well as further lacquer or film formers known to the skilled artisan. In some embodiments, the film forming polymer is present at a concentration of about 1-5% w/v, e.g. about 2-4% w/v.

The transdermal film may also include a penetration/permeation enhancer. Permeation enhancers are molecules that interact with the constituents of the skin's outermost and rate limiting layer stratum corneum (SC), and increase its permeability. In a preferred embodiment, the formulation of the disclosure utilizes citral as a permeation enhancer. Citral, or 3,7-dimethyl-2,6-octadienal or lemonal, is either a pair, or a mixture of terpenoids with the molecular formula $C_{10}H_{16}O$. The two compounds are geometric isomers. The E-isomer is known as geranial or citral A. The Z-isomer is known as neral or citral B. In some embodiments, the permeation enhancer is present at a concentration of about 1-5% w/v, e.g. about 2-4% w/v.

Additional skin penetration enhancers which may be incorporated into the transdermal film include, but are not limited to, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG), and surfactants.

The transdermal film may also include a plasticizer. The plasticizer preserves elasticity and drug stability, avoids films' cracking, and enhances drug permeation. In a preferred embodiment, the formulation of the disclosure utilizes propylene glycol as a plasticizer. In some embodiments, the plasticizer is present at a concentration of about 1-5% w/v, e.g. about 2-4% w/v. Other suitable plasticizers include, but are not limited to, phthalate esters, phosphate esters, fatty acid esters, polyethylene glycol, and other glycol derivatives.

The compositions of the present disclosure may also contain other components such as, but not limited to, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight.

In an embodiment, a composition of the present disclosure includes at least one bioadhesive polymer. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also include methods of preparing transdermal films loaded with transfersomes. Transfersomes may be prepared by methods known in the art. In some embodiments, transfersomes are prepared by a thin lipid film hydration technique. In this method, the dried lipid film is hydrated with a specific pH buffer and sonicated for a specified time using a probe sonicator. In some embodiments, the transfersomes are present in a hydration medium at a pH of 7-9, e.g. 7.5-8.5. The hydrating medium may comprise either water or saline phosphate buffer. The pH of the hydration medium keeps the drug unionized to increase the entrapment and permeation of the drug. The transfersomes are then mixed with a film-forming polymer, a penetration enhancer, and a plasticizer to produce a gel. The gel preparation may then be poured onto a contained surface, e.g. a petri dish, to allow for complete evaporation of water and formation of the film. In some embodiments, the method further comprises attaching a backing membrane to the film. The film may be incorporated into known transdermal delivery devices, e.g. in a patch containing an adhesive for application to the skin.

The present disclosure also provides a method of delivering an active agent by topically administering a transdermal film as described herein. Further embodiments provide a method of treatment of a human or non-human animal subject by delivery of an active agent as hereinbefore defined. Further embodiments provide a method of enhancing the bioavailability of the active agent by topically applying a transdermal film formulation as described herein to the skin of the subject.

The compositions and dosage forms of the disclosure may be useful for the treatment of any disease or disorder that the included active agent is useful for treating. For example, if avanafil is used, the composition or dosage form may be useful for the treatment of cardiovascular disorders or erectile dysfunction.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. avanafil) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type.

In an embodiment, the composition or dosage form of the disclosure is applied topically to any body surface, including the skin and all other epithelial or serosal surfaces. However, whilst the beneficial effects of the disclosure are particularly apparent in transdermal delivery, the utility of the disclosure is not limited and the formulations according to the invention may also be administered parenterally or enterally, eg. as implants or by intravenous, intramuscular or subcutaneous injection, by infusion, or orally.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Summary

Avanafil (AVA) is a Class II drug according to the Biopharmaceutical Classification System (BCS). Its dissolution is the rate-limiting step for absorption which is also altered in the presence of food and in facing the first-pass metabolism. So, our study aimed to overcome the previous hurdles and improve the bioavailability of AVA by its incorporation in the ultra-deformable nanovesicles, transfersomes (TRF), then loading these nanovesicles in transdermal films. The AVA-loaded TRF formulation was optimized using Draper-Lin small composite design. The optimized AVA-loaded TRF was evaluated for vesicle size, polydispersity index, zeta potential, the efficiency of drug entrapment, and in vitro drug release. The optimized AVA-loaded TRF film was assessed for skin permeation using a fluorescence laser microscope and for pharmacokinetic parameters after a single dose application on the rats. The optimized AVA-loaded TRF showed a vesicle size of 97.75 nm, a zeta potential of −28.83 mV, and entrapment efficiency of 95.14% with good deformability and release profile. The intense discoloration in the deep skin layers of the rats indicated the permeation efficiency in comparison with raw AVA-loaded films. The pharmacokinetic parameters specified the augmented absorption extent of the drug following transdermal application of the optimized AVA-loaded TRF film when compared with raw AVA film. These results open the field for wider clinical application of this alternative delivery pathway for improved bioavailability, efficacy as well as patient compliance and satisfaction.

Materials and Methods

Materials

Avanafil powder was obtained from Jiangsu Oubo Biological Technology Company (Changzhou, China). Sorbitan monolaurate (Span 20), sorbitan monostearate (span 65), sorbitan monooleate (Span 80), sorbitan trioleate (Span 85), polysorbate 80 (Tween 80), acetic acid, methanol, and citral were purchased from Sigma-Aldrich (St. Louis, Mo.). Purified soybean lecithin with a phosphatidylcholine content of at least 90% (Phospholipon 90 G) was kindly supplied by Lipoid GmbH (Koln, Germany). Hydroxypropyl methylcellulose 4000 cp (HPMC 4000) was obtained from Spectrum Chemical Manufacturing Corporation (Gardena, Calif.). Propylene glycol and clove oil were purchased from TEDIA Company, Inc. (Ohio, USA). All other materials were of analytical grade and used without any further purification.

Design of Experiments

The Draper-Lin small composite design was used to explore the effect of the chosen independent variables on the formulation of AVA-loaded TRF. These independent variables include phospholipid to drug molar ratio ($X_1$), surfactant HLB ($X_2$), hydration medium pH ($X_3$), and sonication time ($X_4$). The study aimed to investigate the effect of these factors on vesicle size ($Y_1$), zeta potential ($Y_2$), and the EE % ($Y_3$). Statgraphics® 18 Centurion Software (VA, USA) was utilized to statistically analyze the obtained data and suggest the optimum level of the variable that maximizes the desirability function within the design space. The dependent and independent factors and their levels are listed in Table 1. A total of 18 formulations have been suggested and recorded in Table 2. The order of the experiments has been entirely randomized for protection from the effects of the lurking variables.

TABLE 1

Independent variables used in Draper-Lin small composite design in the formulation of AVA-loaded TRF

| Independent variables | Lower extreme (−1.68) | Low Level (−1) | Medium Level (0) | High Level (+1) | Higher extreme (1.68) |
|---|---|---|---|---|---|
| Phospholipid to drug ratio ($X_1$) | 1.64:1 | 2:1 | 3.09:1 | 4:1 | 5.47:1 |
| Surfactant HLB ($X_2$) | 2.834 | 4.3 | 6.45 | 8.6 | 10.06 |
| Hydration medium pH ($X_3$) | 5.51 | 6.2 | 7.2 | 8.2 | 8.88 |
| Sonication time ($X_4$), (s) | 79.09 | 120 | 180 | 240 | 280.90 |

TABLE 2

Independent and dependent factors of AVA-loaded TRF based on Draper-Lin small composite design

| Formulation | Independent factors | | | | Dependent factors | | |
|---|---|---|---|---|---|---|---|
| code | $X_1$ | $X_2$ | $X_3$ | $X_4$ (s) | $Y_1$ (nm) | $Y_2$ (mV) | $Y_3$ (%) |
| F-1 | 2:1 | 8.6 | 6.2 | 240 | 303.7 ± 12.91 | −2.19 ± 0.19 | 97.32 ± 0.13 |
| F-2 | 3.09:1 | 10.06 | 7.2 | 180 | 530.7 ± 31.90 | −4.27 ± 0.22 | 92.38 ± 0.29 |
| F-3 | 3.09:1 | 6.45 | 7.2 | 280.90 | 198.6 ± 1.732 | −9.86 ± 0.49 | 93.36 ± 0.08 |
| F-4 | 4:1 | 4.3 | 8.2 | 240 | 254.9 ± 24.91 | −27.37 ± 0.7 | 92.63 ± 0.38 |
| F-5 | 2:1 | 4.3 | 8.2 | 120 | 287.3 ± 75.10 | −29.13 ± 0.6 | 99.8 ± 0.30 |
| F-6 | 4:1 | 8.6 | 8.2 | 120 | 370.46 ± 17.3 | −14.1 ± 0.43 | 91.33 ± 0.37 |
| F-7 | 2:1 | 8.6 | 8.2 | 240 | 350.06 ± 22.0 | −15.6 ± 0.43 | 97.18 ± 0.15 |
| F-8 | 3.09:1 | 6.45 | 7.2 | 79.09 | 195.80 ± 6.61 | −8.39 ± 0.54 | 92.13 ± 0.21 |
| F-9 | 3.09:1 | 6.45 | 5.51 | 180 | 170.26 ± 3.15 | −1.12 ± 0.07 | 95.32 ± 0.62 |
| F-10 | 2:1 | 4.3 | 6.2 | 120 | 249.1 ± 17.46 | −3.21 ± 0.54 | 98.43 ± 0.17 |
| F-11 | 3.09:1 | 6.45 | 8.88 | 180 | 259.6 ± 3.17 | −28.57 ± 0.07 | 96.00 ± 0.04 |
| F-12 | 5.47:1 | 6.45 | 7.2 | 180 | 156.7 ± 11.58 | −29.93 ± 0.16 | 92.47 ± 0.59 |
| F-13 | 4:1 | 4.3 | 6.2 | 240 | 138.23 ± 3.20 | −2.00 ± 0.51 | 90.49 ± 2.08 |
| F-14 | 4:1 | 8.6 | 6.2 | 120 | 222.00 ± 3.81 | −2.28 ± 0.53 | 90.52 ± 0.13 |
| F-15 | 3.09:1 | 2.83 | 7.2 | 180 | 102.8 ± 13.2 | −14.87 ± 0.8 | 97.79 ± 0.06 |
| F-16 | 1.64:1 | 6.45 | 7.2 | 180 | 383.2 ± 32.76 | −8.88 ± 0.35 | 95.38 ± 0.18 |
| F-17 | 3.09:1 | 6.45 | 7.2 | 180 | 205.9 ± 24.58 | −9.52 ± 0.26 | 93.79 ± 0.21 |
| F-18 | 3.09:1 | 6.45 | 7.2 | 180 | 220.20 ± 4.78 | −9.46 ± 0.44 | 93.54 ± 0.36 |

Notes:
Values are considered as average ± standard deviation (n = 3)
Abbreviations:
$X_1$ is phospholipid to drug molar ratio,
$X_2$ is the surfactant HLB,
$X_3$ is the hydration medium pH,
$X_4$ is the sonication time,
$Y_1$ is the particle size,
$Y_2$ is the zeta potential and
$Y_3$ is the entrapment efficiency.

Preparation of AVA-Loaded TRF

AVA-loaded TRF was prepared by the thin lipid film hydration technique as previously reported with slight modification [12,14]. Briefly, specific weights of AVA, Phospholipon 90 G, and surfactant were dissolved in a round bottom flask containing methanol by the aid of a water bath sonicator (QS3, Ultrawave Ltd, Cardiff, UK) for 5 min to ensure dissolving all the components. The surfactant was added in the ratio of 1:3 of Phospholipon 90 G in all formulations.

The obtained dispersion was subjected to rotary evaporation (R-200, Buchi labortechink AG, Flawi, Switzerland) under reduced pressure at 50° C. until the complete formation of a thin film on the flask wall. This film was maintained overnight in a vacuum oven (model 6505, Thermo Fisher Scientific, OH, USA) to confirm the complete removal of methanol. The dried lipid film was hydrated with 30 ml of specific pH buffer depending on the pH medium of each formulation in the study design. Finally, all formulations were sonicated for a specified time as suggested by the design using a probe sonicator (VCX 750, Sonics & Materials, Inc., CT, USA) with 3 freeze-thaw cycles interspersed for 10 minutes to confirm the conversion of the multilamellar vesicles to small unilamellar ones with minimum vesicular size.

Evaluation of AVA-Loaded TRF

Determination of Vesicle Size, Polydispersity Index, and Zeta Potential

Particle size (PS), polydispersity index (PDI), and zeta potential (ZP) were measured by the dynamic light scattering technique (DLST) using Malvern zetasizer ZSP (Malvern, United Kingdom). An aliquot from each formulation dispersion was diluted with distilled water. The sample was subjected to three measurements and the average was calculated.

Measurement of the Entrapment Efficiency % (EE %)

The efficiency of the prepared vesicles to entrap AVA was measured by the indirect method as reported before [20]. Free AVA in each formulation was calculated from the sample's supernatant. Half milliliter from each formulation dispersion was centrifuged at 15000 rpm at 8° C. for one hour to separate the entrapped portion of AVA from the free one. One hundred microliters of supernatant were diluted with the same volume of methanol and then analyzed by High-Performance Liquid Chromatography (HPLC) to determine the free AVA in the sample. EE % was calculated from equation (1).

$$EE\ (\%) = \frac{\text{Total amont of } AVA \text{ loaded in transfersomes} - \text{free } AVA \text{ in the supernatant}}{\text{Total amount of } AVA \text{ loaded in transfersomes}} \times 100 \qquad \text{(equation 1)}$$

Chromatographic Analysis for the Measurement of AVA EE %

The free AVA was measured using an in-house developed and validated chromatographic analysis [21]. The separation was performed using HPLC Agilent 1200 LC Quaternary series pump coupled with Agilent 1200 high-performance autosampler (Agilent Technologies Inc., CA, USA). The elution was carried by the ThermoRP-C18 column with a flow rate of 1.2 ml/min DAD-detector at a wavelength of 230 nm. The mobile phase was composed of 0.1M ammonium acetate buffer pH 2.5, methanol, and acetonitrile with a 20:40:40 v/v/v ratio at room temperature. The limit of quantitation was 1 µg/ml and the linearity was ranged from 10-1000 µg/ml. The recovery percent for the concentrations ranged from 99.01% to 100.91%.

In Vitro Drug Release Study

In vitro release study of AVA-loaded TRF was carried out by using the dissolution apparatus USP apparatus II (Erweka GmbH, Heusenstamm, Germany). Three predetermined known weights from each formulation were tested. They were performed in an open-ended cylindrical tube with one end tied with a dialysis membrane. In the dissolution apparatus, each sample suspended in a 1-liter receptor medium of phosphate buffer of pH 7.2 with 1.5 g tween 20 to confirm the sink condition of the dissolution process and rotated at 75 rpm 37±1° C. A small volume was withdrawn from each receptor compartment at predetermined time intervals of 0.5, 1, 2, 3, 4, 6, 9, 12, and 24 hours and analyzed for its AVA content using the previously mentioned HPLC method. The withdrawn samples were compensated with the same volume of a fresh preheated medium.

Prediction, Preparation, and Characterization of the Optimized Formulation

Draper-Lin small composite design was successfully adopted, and the experiments were designed by choosing the dependent variables with the selected levels. Response surface methodology evolved for responses showed the effect of each parameter and its interaction with other parameters which was utilized for predicting and obtaining the optimized AVA-loaded TRF formulation using Statgraphics software. The optimized formulation was prepared and evaluated by measuring its vesicle size, zeta potential, and EE %.

Evaluation of Optimized AVA-Loaded TRF

Deformability of the Optimized AVA-Loaded TRF

The deformability (elasticity index) of the optimized formulation was performed according to the extrusion method [22]. Samples of the optimized formulation were extruded through a 0.1 µm membrane filter under reduced pressure of less than 1.2 Mpa. The elasticity of the vesicle was calculated by equation 2.

$$\text{Elasticity (\%)} = \frac{TRF \text{ size before extrusion} - TRF \text{ size after extrusion}}{TRF \text{ size before extrusion}} \times 100 \qquad \text{(equation 2)}$$

Transmission Electron Microscope Imaging of TRF

The prepared TRF was investigated by Transmission electron microscopy (TEM). On a carbon-coated grid, a few drops of the prepared formulation were placed, left for about 3 min to improve vesicle adsorption on a carbon film, and the excess liquid was then extracted by using a filter paper. One drop from a 1% aqueous solution of phosphotungstic acid was added and the sample was examined under TEM with a magnification of 10,000-100,000 with an acceleration voltage of 80 kV.

Preparation of AVA-Loaded TRF Film

To prepare AVA-loaded TRF film, the accurate weight of film-forming polymer HPMC (2% w/v) was dispersed in a specified volume of optimized AVA dispersion placed over magnetic stirring. The polymeric solution was mixed with citral as a penetration enhancer (2% w/v) and propylene glycol as a plasticizer (2% w/v). The prepared AVA polymeric solution was left for 24 h in the refrigerator at 4° C. to obtain a clear gel. The prepared gel was then poured into 9-cm diameter silicon-coated Petri dishes for easier removal of films. Petri dishes were then kept in an oven at 40° C. until complete evaporation of water. The formed film was covered with a backing membrane and cut into an 8 $cm^2$ strip containing TRF with an AVA content equivalent to 0.75 $mg/cm^2$ with a uniform thickness, packed in Al-foil, and stored in a desiccator [23]. For comparison, raw AVA films with the same amount of AVA, HPMC, citral, and propylene glycol were prepared with the same previously mentioned method.

Evaluation of AVA-Loaded TRF Film

Content Uniformity

Three cut strips of AVA-loaded TRF film (8 $cm^2$) supposed to contain 6 mg AVA were separately transferred into graduated glass stopper flasks containing 100 ml of methanol. In the shaking water bath, the flasks were kept at 25° C. for 72 hours. The drug content was estimated using the HPLC method mentioned above after the filtration of the obtained dispersions.

Thickness Uniformity

At three different points in AVA-loaded TRF film, the thickness of the prepared films was measured by using a digital micrometer Mitutoyo Co, and the average thickness was determined.

Elongation Percent

To evaluate the maximum elongation of the AVA-loaded TRF films concerning the original length, the percent elongation was calculated by applying a specific weight or force. This evaluation was assessed with an elongation mechanical test apparatus built in our laboratory and according to the procedure previously reported [24]. In the elongation apparatus, there were two clamps: the top one is fixed in place, while the bottom clamp moves free and is linked to a specific weight. Between the two clamps, a rectangular strip of AVA-loaded TRF film (1×4 cm) was placed by 2 cm and a constant weight fixed to the bottom clamp. The change in film length was measured after 5 min and the percentage elongation was determined using equation 3.

$$\text{Elongation (\%)} = \frac{L_f - 2}{2} \times 100 \qquad \text{(equation 3)}$$

where $L_f$ is the final length of each film. The same procedure was carried on three strips of film and the average was calculated.

Visualization of Skin Permeation for the Optimized AVA-Loaded Transdermal Film Using a Fluorescence Laser Microscope Fluorescein isothiocyanate (FITC)-dextran as a permeability tracer (0.15 μmol/mL) was used instead of AVA in the preparation of the optimized AVA-loaded transdermal film [25]. FITC-dextran-loaded TRF films were added to the rat skin, and the permeation of FITC-dextran across the rat skin was investigated. Transdermal film loaded with raw FITC-dextran (control), that is, no TRF included, was prepared, and treated as described for the labeled optimized transdermal film. The treated skin was removed after 1, 3, and 5 hours and kept in 10% buffered formalin as a fixative [26]. Blocks of skin samples (paraffin wax sections of 4 μm thickness) were prepared using a microtome. The prepared samples were observed using Zeiss Axio Observer D1 Inverted Dic Fluorescence Microscope (Carl Zeiss AG, Oberkochen, Germany) The filter used was 470/40 nm excitation, 495 beam splitter, and 525/50 nm emission Images were acquired with identical acquisition parameters, with minimum excitation and gain.

In Vivo Pharmacokinetic Studies

Study Design

The study used a single-dose one-period parallel design. The study was performed following EMA, International Conference on Harmonization (ICH), Good Clinical Practice (GCP), and US-FDA guidelines. The animal experimental protocol was revised and approved by the Research Ethics Committee, Faculty of Pharmacy, King Abdulaziz University (Approval No. PH-119-41). The study fulfilled with the Declaration of Helsinki, the Guiding Principle in Care and Use of Animals (DHEW production NIH 80±23), and the "Standards of Laboratory Animal Care" (NIH distribution #85±23, reconsidered in 1985).

Animal Handling

Twenty-four male Wistar rats, weighing between 250 and 300 g were used in this study. The rats were housed in a cage and maintained on a 12 h light/dark at room temperature (25° C.) and relative humidity of 55±10%, with free access to water and ad libitum. General and environmental conditions were strictly monitored. All animals were divided randomly into 2 groups (12/group). Group I (Reference group, 12 animals that were divided into 2 sub-groups for blood sampling by alternative method) received topically 20 mg/kg dose of raw AVA-loaded film. Group II (Test group, 12 animals that were divided into 2 sub-groups for blood sampling by alternative method) received topically 20 mg/kg dose of the optimized AVA-loaded TRF film. The film was applied on the dorsal surface of each test animal after the removal of hair using hair remover.

Blood Sampling

Blood samples (250 μL) were collected in heparinized Eppendorf tubes via the oculi choroidal vein at 0.5, 1.0, 2.0, 4.0, 8.0, 12.0, and 24.0 h after the application of the film under light ether anesthesia. Animals were allowed free access to food and drinking water between time points of blood collection to avoid dehydration. Plasma samples were obtained at 2850×g for 5 min and frozen at −20° C. until an analysis was performed. AVA concentrations were measured using the HPLC method.

Pharmacokinetics Parameters Evaluation

Pharmacokinetic parameters of the optimized AVA-loaded TRF film were evaluated in comparison with the raw AVA-loaded film on male Wistar rats. Both formulations were applied topically as described in the animal handling section. The concentration of AVA versus time and the analysis of the pharmacokinetic parameters were determined by the non-compartmental extravascular pharmacokinetic model using PKsolver (An add-in program for pharmacokinetic data). Maximum (peak) plasma concentration over the period specified ($C_{max}$), and time point of maximum plasma concentration ($T_{max}$), area under the plasma concentration-time curve from zero time to the last measurable concentration ($AUC_{0\text{-}t}$) was calculated by the linear trapezoidal method and area under the plasma concentration-time curve from time zero to infinity ($AUC_{0\text{-}inf}$) was calculated as the sum of the $AUC_{0\text{-}t}$ plus the ratio of the last measurable plasma concentration to the elimination rate constant and the area under the first moment of the plasma concentration-time curve from time zero to infinity ($AUMC_{0\text{-}inf}$) Also, the individual estimate of the terminal elimination rate constant (Lambda_z), the mean residence time ($MRT_{0\text{-}inf}$) which is calculated by the ratio of AUMC to AUC, and elimination half-life ($t_{1/2}$) which was calculated as 0.693/Lambda_z. Moreover, the apparent total body clearance of the drug from plasma after oral administration (Cl/F) was calculated by dividing the dose by AUC and the apparent volume of distribution during the terminal phase after non-intravenous administration (Vz/F) was calculated by multiplying total body clearance by MRT. Finally, the relative bioavailability of the optimized formula (AUC test/AUC reference×100) was determined.

Chromatographic Conditions

The concentration of AVA in plasma samples was determined using Parkin Elmer equipped with a variable wavelength ultraviolet spectroscopic detector adjusted at 230 nm along with a quaternary pump, autosampler, vacuum degasser, and Winchrom software. Chromatographic separation was performed on a Phenomenex, RP Hi-Q-Sil C18, 250 mm×4.6 mm, 5 μm column (Phenomenex, Torrance, Calif.) at room temperature. The mobile phase was composed of acetonitrile and methanol in a 0.05 M ammonium acetate buffer, pH 3 (30:20:50 v/v/v). The mobile phase was pumped at a flow rate of 1.5 ml/min. For AVA extraction from plasma samples, 0.5 mL a mixture of acetonitrile-methanol (1:1) was added, vortexed for 1 minute, and then centrifuged for 10 minutes at 5000 rpm. The organic phase was taken and injected 40 μl into the HPLC. The internal standard (100 ng/ml sildenafil solution in the mobile phase) was prepared by dissolving 10 mg accurately weighed of the compound in 100 ml of acetonitrile. The developed bioanalytical chromatographic method was in-house validated and deemed precise, accurate, sensitive, selective, and robust. The limits of quantitation and detections were 2 and 0.5 ng/ml, respectively.

Statistical Analysis

All statistical analyses were performed using GraphPad Prism 8 for Windows, Version 8.2.1 Software (San Diego, Calif., USA). Regarding the plasma concentration-time curve, Two-way ANOVA followed by Sidak's multiple comparisons test was done to compare each means with the other at all time points and assess the significance between groups. Finally, a two-tailed unpaired t-test was used to assess the pharmacokinetic parameters of the formulations. Results with $P<0.05$ were considered significant.

Results and Discussion

Initial Studies

The loading of AVA in TRF and one process factor as well as one formulation factor that influences this loading process were initially studied. The process factor was the sonication method applied while the formulation factor was the hydrophilic-lipophilic balance (HLB) of the surfactant used. This step is very important to detect which one of both factors is more suitable for improving the quality attributes of the produced vesicles. Either a water bath sonicator or probe sonicator was used for the preparation of AVA-loaded TRF. On the other hand, two surfactants such as span 65 or tween 80 with HLB values of 2.1 and 15, respectively were used as edge activators to represent the low and the high values of surfactant HLB could be used. Based on the screening of the HLB value of surfactants used, all formulations were divided into two groups. The first group utilized span 65 as an edge activator in preparation of two formulations and sonicated using a water bath sonicator for a period of 30 and 60 minutes. Unlikely, the vesicle size average for both formulations were 778.8 and 823.7 nm, and the zeta potential was −20.1 and −17.1 mV, respectively. The same formulation when sonicated with a probe sonicator with the freeze-thaw cycles revealed an average particle size of 291.6 nm and zeta potential of −13.1 mV. The second group of formulations utilized tween 80 instead of span 65 as an edge activator and sonicated using a water bath sonicator for a period of 30 and 60 min. This group displayed a decrease in the particle size average of 378.2 and 266.9 nm, and zeta potential was −11.9 and −12.4 mV, respectively. While using a probe sonicator with freeze-thaw cycles the particle size average of 363.3 and 241.2 nm, and the zeta potential was −9.28 and −9.04 mV, respectively. From the obtained results, the probe sonicator was selected as the method of choice in the preparation of AVA-loaded TRF as it gave the smallest size of vesicles.

Evaluation of AVA-Loaded TRF

According to the Draper-Lin small composite design with considering the independent variables previously mentioned in Table 1, all prepared formulations gave vesicles that differ in their size, PDI, zeta potential, and EE %. Table 2 showed that the vesicle size was varied from 102.8±13.2 nm to 530.7±31.90 nm for F15 and F2, respectively. The values of PDI for all formulations ranged from 0.383 for F13 to 0.758 for F18. While, the zeta potential ranged from −1.12±0.07 for F9 to −29.93±0.16 for F12. The percentage fraction of the total drug entrapped in the TRF is ranged from 90.49±2.08% for F13 to 99.8±0.30% for F5, respectively.

In Vitro Drug Release Study

Figure 1B:
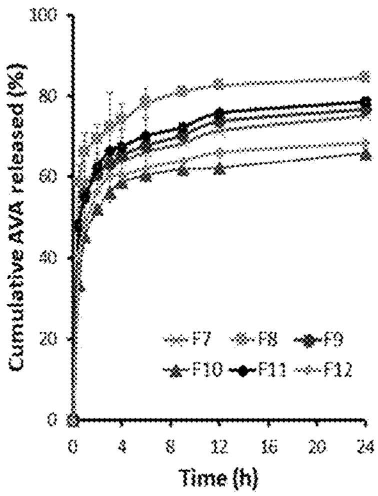
Figure 1C:
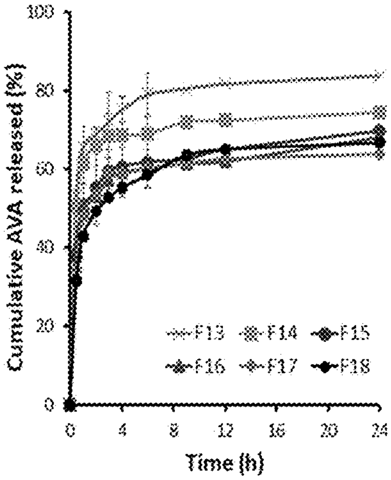

The release profiles of Draper-Lin small composite design formulations (F1-F18) were presented in FIG. 1(*a-c*). The cumulative percent of AVA from all formulations was ranged from 63.85% in F17 to 84.59% in F8 over 24 h. The release of AVA from TRF preparations showed a biphasic release pattern. An initial rapid release phase (>40%) was observed in the first 0.5 h followed by a sustained release phase that lasts for the rest 24 h of the study period. The rapid initial release phase may be attributed to the fraction of the drug adsorbed on the surface of the prepared TRF. These findings are consistent with the previous study that also identified the profile of biphasic release from ultradeformable vesicles of diclofenac sodium [27]. Also, it was noticed that the formulations of low EE % showed the highest cumulative drug release. This relationship observed in F2, F3, F4, F6, F8, F13 and F14 which have EE % of 92.38, 93.36, 92.63, 91.33, 92.13, 90.49 and 90.52%, respectively and show cumulative release of 74.02, 72.2, 76.51, 79.55, 84.59, 83.8 and 74.41%, respectively. A similar finding was reported with proniosomes for transdermal delivery of vinpocetine conducted by El-laithy and co-workers [28]. According to the obtained results, there is a direct relationship between the HLB of surfactant in preparation and the cumulative release. As the HLB value increased from 2.83 to 10.06, the cumulative release increased from 69.7% (F15) to 74.02% (F2) at an equal level of $X_1$ and $X_3$ as reported in different studies that conducting on niosomal vesicles prepared by different surfactants [29][30]. Also, It was found that the cumulative AVA release increased with increasing phospholipid to drug molar ratio from 2:1 to 4:1. The formulations with ratio 2:1 displayed a lower cumulative release from 66.07 to 75.29% while the formulations with ratio 4:1 displayed a higher cumulative release from 74.41 to 83.8%. This finding was in agreement with a previous study conducted on liposomal vincristine formulations that investigated the drug release based on the variation in the drug-to-lipid ratio [31].

Optimization of AVA-loaded TRF

Statgraphics® 18 Centurion Software (VA, USA) was used to statistically analyze the effect of $X_1$, $X_2$, $X_3$, and $X_4$ on $Y_1$, $Y_2$, and $Y_3$ through the multiple regression analysis and one-way analysis of variance. For the studied variables in the study design, values of estimated effect, F-ratio, and associated P-value have calculated as well as their interactions and quadratic effects on obtained responses as illustrated in Table 3. So, the estimate of a positive sign indicates the direct relationship between the variable and the studied response while the estimate of a negative sign indicates the inverse relationship. F-ratio compares between the observed and expected variation of variable averages where an F-ratio that is greater than 1 is an indication of a location effect and hence the P-value reports a significant level. The independent factor has a significant effect on the studied response when the P-value less than 0.05. Besides, the statistic value of R-squared which indicates the variability in each studied response was calculated as well as the statistic value of adjusted R-squared that more suitable for comparing models with different numbers of independent variables.

TABLE 3

Statistical analysis with the estimated effects of factors, F-ratio, and associated P-values for AVA TRF formulation particle size ($Y_1$), zeta potential ($Y_2$), and entrapment efficiency ($Y_3$).

| | Vesicle size ($Y_1$), nm | | | Zeta potential ($Y_2$) mV | | | Entrapment Efficiency ($Y_3$), % | | |
|---|---|---|---|---|---|---|---|---|---|
| Factors | Estimated effect | F-ratio | P-ratio | Estimated effect | F-ratio | P-ratio | Estimated effect | F-ratio | P-ratio |
| $X_1$ | −134.67 | 64.37 | 0.0040* | 12.516 | 28.18 | 0.0131* | −1.730 | 33.17 | 0.0104* |
| $X_2$ | 254.42 | 229.7 | 0.0006* | −6.302 | 7.15 | 0.0755 | −3.216 | 114.6 | 0.0017* |
| $X_3$ | 73.293 | 46.03 | 0.0065* | 17.966 | 140.1 | 0.0013* | 0.779 | 16.26 | 0.0274* |
| $X_4$ | 1.6649 | 0.01 | 0.9272 | 0.8740 | 0.14 | 0.7355 | 0.731 | 5.93 | 0.0930 |
| $X_1 X_1$ | 44.444 | 14.58 | 0.0316* | 5.3597 | 10.74 | 0.0465* | 0.227 | 1.19 | 0.3554 |
| $X_1 X_2$ | 22.022 | 1.01 | 0.3893 | 1.2640 | 0.17 | 0.7091 | 1.346 | 11.76 | 0.0415* |
| $X_1 X_3$ | 45.007 | 10.17 | 0.0498* | −0.535 | 0.07 | 0.8048 | 0.43 | 2.90 | 0.1873 |
| $X_1 X_4$ | 175.12 | 63.76 | 0.0041* | 0.5822 | 0.04 | 0.8621 | −1.966 | 25.10 | 0.0153* |
| $X_2 X_2$ | 77.534 | 44.36 | 0.0069* | −1.594 | 0.95 | 0.4014 | 1.047 | 25.27 | 0.0152* |
| $X_2 X_3$ | 10.122 | 0.51 | 0.5251 | −6.515 | 10.80 | 0.0462* | −0.71 | 7.90 | 0.0673 |
| $X_2 X_4$ | −83.400 | 14.46 | 0.0319* | 13.611 | 19.52 | 0.0215* | 5.209 | 176.1 | 0.0009* |
| $X_3 X_3$ | 5.5387 | 0.23 | 0.6667 | 2.1353 | 1.71 | 0.2827 | 1.453 | 48.69 | 0.0060* |
| $X_3 X_4$ | −5.7725 | 0.17 | 0.7100 | 0.26 | 0.02 | 0.9040 | −0.045 | 0.03 | 0.8700 |
| $X_4 X_4$ | −6.9982 | 0.36 | 0.5901 | −1.9093 | 1.36 | 0.3273 | −0.607 | 8.49 | 0.0618 |
| $R^2$ | | 99.348 | | | 98.641 | | | 99.71 | |
| Adj-$R^2$ | | 96.306 | | | 92.301 | | | 98.39 | |
| SEE | | 19.961 | | | 2.8039 | | | 0.357 | |
| MAE | | 6.7626 | | | 0.9900 | | | 0.117 | |

Note:
*Significant effect of a factor on individual response.
Abbreviations:
$X_1$ = phospholipid to drug molar ratio;
$X_2$ = Surfactant hydrophilic lipophilic balance;
$X_3$ = Hydration medium pH;
$X_4$ = Sonication time;
$X_1X_2$, $X_1X_3$, $X_1X_4$, $X_2X_3$, $X_2X_4$, and $X_3X_4$ are the interaction terms between the factors;
$X_1X_1$, $X_2X_2$, $X_3X_3$, and $X_4X_4$ are the quadratic terms between the factors;
$R^2$ = R-squared;
Adj-$R^2$ = adjusted R2;
SEE = standard error of estimate;
MAE = mean absolute error.

Effect of the Variables on the Vesicle Size

Figure 2A:
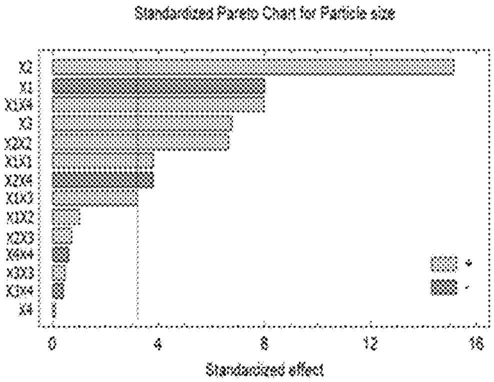
FIGS. 2A-D. Effect of the variables on the vesicle size of AVA-loaded TRFs; a) standardized Pareto chart; b-d) Response surface plots.

According to the results of the statistical analysis shown in Table 3, the vesicle size of AVA-loaded TRF is significantly affected by the positive effect of $X_2$ and $X_3$, the quadratic terms of $X_1$ and $X_2$, and the interaction terms of $X_1X_4$ and $X_1X_3$. While $X_1$ and the interaction term of $X_2X_4$ have significant negative antagonistic effects on $Y_1$. Also, it was found that R-squared and adjusted R-squared statistical values were 99.348% and 96.307%. The effect of the studied variables on $Y_1$ was confirmed by the statistical analysis results of the standardized Pareto chart as illustrated in FIG. 2*a*. This chart includes a P-value of 0.05 vertical reference line. Any effect which goes beyond this vertical line is statistically considered to be significant [32]. The equation of the fitted model was indicated in equation 4.

$$\text{Vesicle size } (Y_1)=8162.29-152.15X_1-64.132X_2-257.366X_3-13.261X_4+0.500X_1^2+0.768X_1X_2+3.376X_1X_3+0.218X_1X_4+8.386X_2^2+2.354X_2X_3-0.323X_2X_4+2.769X_3^2-0.048X_3X_4-0.009X_4^2 \quad \text{(equation 4)}$$

Figure 2B:
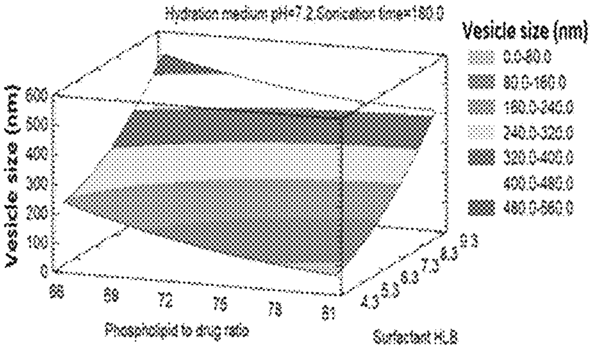
Figure 2C:
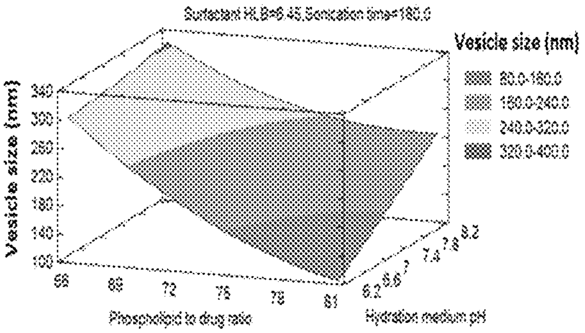
Figure 2D:
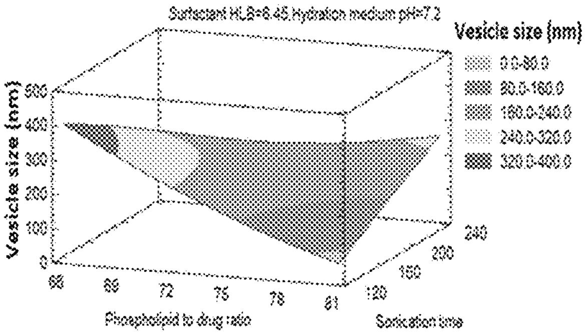

To explain the negative effect of phospholipid to drug molar ratio ($X_1$), the response surface plots were constructed as shown in FIGS. 2*b-d*). The size of TRF decreased with an increasing value of $X_1$ from 2:1 to 4:1 as that observed in F1, F5, and F10 with sizes of 303.7, 287.3, and 249.1 nm, respectively to 222, 254.9, and 138.23 nm in F14, F4, and F13, respectively at the same level of $X_2$ and $X_3$. Also, it was observed that the vesicle size decreased from 383.2 nm in F16 to become 156.7 nm in F12 when the phospholipid to drug molar ratio increase from 1.64:1 to 5.47:1 at an equal level of $X_2$ and $X_3$. This finding was in agreement with those found in a previous study on niosomal gel system loaded with ursolic acid [33]. In contrast, many researchers found the increase of the phospholipid content in the vesicle increases the vesicle size. For example, Ahmed and his partners found the size of ethosomal nanovesicle of glimepiride increased with increasing the phospholipid percentage. Surface charges of the nanovesicles and the drug and the arising repulsive and attractive forces between the vesicle and the drug may be behind the variation of the vesicle size. AVA, which has a negative charge, undergoes repulsion with the negative charge of Phospholipon® 90 G resulting in the disaggregation of particles thus ensuring its size reduction. On the contrary, glimepiride which has a positive charge undergoes attraction with a negative charge of Phospholipon® 90 G resulting in aggregation of particles thus ensuring its size enlargement. Also, the surfactant HLB ($X_2$) showed a positive significant effect on the vesicle size as displayed in the response surface plots FIG. 2*b*. This direct relationship between surfactant HLB value ($X_2$) and the size of TRF that was observed in formulations (F4, F5, F10, and F13) with a ratio of 2:1 of phospholipid to the drug which revealed sizes of 254.9, 287.3, 249.1, and 138.23 nm, respectively. While the formulations (F6, F7, F1, and F14) of a ratio of 4:1 revealed an increase in their sizes to 370.46, 350.06, 303.7, and 222 nm, respectively. The TRF produced with low HLB value (span 80) displayed smaller vesicle sizes than those with high HLB value (tween 80). These findings were in agreement with the previously reported results of TRF formulation for transdermal delivery of pentoxifylline [18] and polyoxyethylene alkyl ether niosomes for delivery of insulin [34]. Besides, the effect of the pH of the hydration medium of AVA TRF dispersion ($X_3$) on the vesicle size showed a direct relationship as illustrated in FIG. 2*c*. As the pH of the hydration medium increased, the vesicle size of the TRF increased. The size increased from 303.7 to 350.06 nm in F1 to F7, respectively when the pH of the hydration medium increased from 6.2 to 8.2 at an equal level of $X_1$ and $X_2$. Also, when the pH of the hydration medium increased from 6.2 to 8.2 as was noticed in F10 to F5, the size increased from 249.1 to 287.3 nm, respectively at the same level of $X_1$ and $X_2$. We also observed an increase in particle size from 138.23 to 254.9 nm for F13 to F4, respectively, and an increase in particle size from 222 to 370.46 nm for F14 to F6, respectively with increasing in the pH of hydration medium from 6.2 to 8.2 at the same level of $X_1$ and $X_2$. Finally, the obtained results revealed that there is no significant effect of the sonication time ($X_4$) on the vesicle size of the prepared TRF.

Effect of the Variables on the Zeta Potential

Figure 3A:
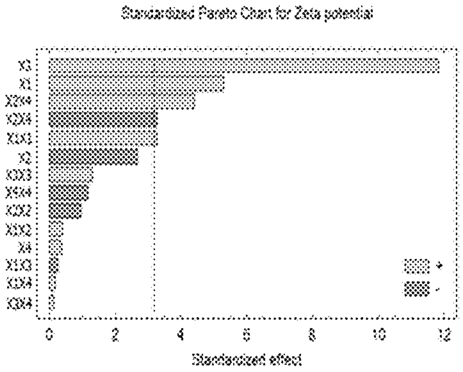
FIGS. 3A-D. Effect of the variables on the zeta potential of AVA-loaded TRFs; a) standardized Pareto chart; b-d) Response surface plots.

The zeta potential of AVA-loaded TRF was significantly affected by $X_1$ and $X_3$, the quadratic term of $X_1$, the interaction terms of $X_2X_3$ and $X_2X_4$ as represented in Table 3. All these variables showed a positive, synergistic effect on $Y_2$ except for $X_2X_3$, which showed a negative, antagonistic effect. This finding was confirmed by the Pareto chart as illustrated in FIG. 3*a*. The R-squared result was found to be 98.64% while the adjusted R-squared statistical values represent 92.30%. The equation of the fitted model was indicated in equation 5.

$$\text{Zeta potential } (Y_2)=252.353-8.035X_1-1.062X_2+5.935X_3-0.306X_4+0.0603X_1^2+0.044X_1X_2-0.040X_1X_3+0.0007X_1X_4-0.172X_2^2-1.515X_2X_3+0.052X_2X_4+1.067X_3^2+0.00216X_3X_4-0.00026X_4^2 \quad \text{(equation 5)}$$

Figure 3B:
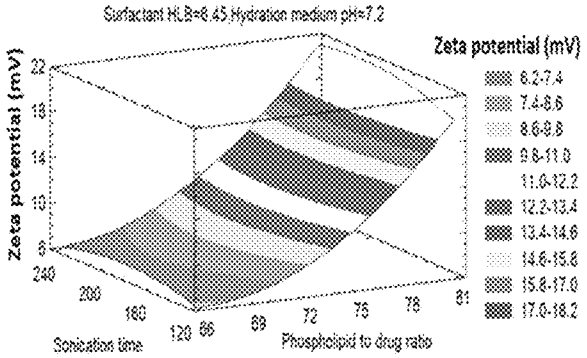
Figure 3C:
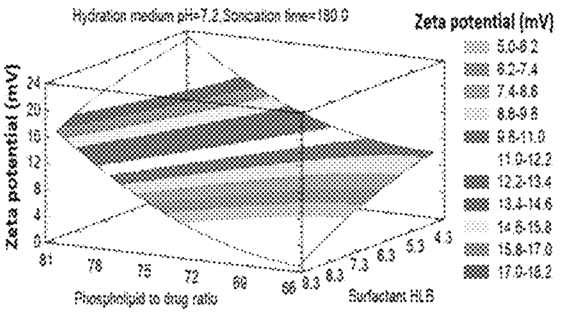
Figure 3D:
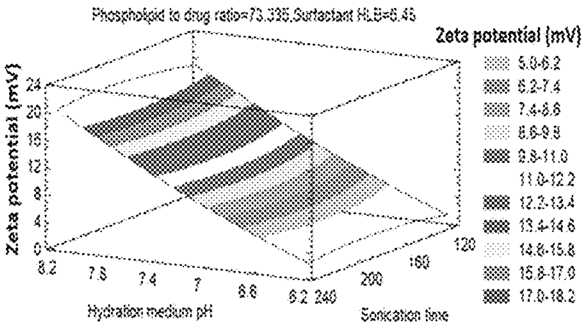

The response surface plots were constructed in FIG. 3*b*&*c*) to demonstrate the positive effect of phospholipid to drug molar ratio ($X_1$) on $Y_2$. According to that, zeta potential increased with increasing value of phospholipid to drug molar ratio ($X_1$) as that observed between F16 and F12 where the zeta potential increase from −8.88 to −29.93 mV as well as between F1 and F14 where the zeta potential increase from −2.19 to −2.28 mV at the same level of $X_2$ and $X_3$ when the phospholipid to drug molar ratio increase from 2:1 to 4:1. This could be attributed to the repulsion between the negative charge of AVA and phospholipid, zeta potential increases with increasing of $X_1$. This finding is in good agreement with the reported results of Das and co-workers in the preparation of clotrimazole vesicles [35]. Also, FIG. 3*d* revealed the positive effect of the pH of the hydration medium ($X_3$) on $Y_2$. It was evident that an increased pH of hydration medium from 6.2 to 8.2 leads to an increase in zeta potential as that demonstrated in F1, F10, F13, and F14 where zeta potential increase from −2.19, −3.21, −2.00, and −2.28 mV to −15.6, −29.13, −27.36 and −14.1 mV in F7, F5, F4, and F6, respectively at the same level of $X_1$ and $X_2$. Smith and co-workers studied zeta potential in the case of cationic, anionic, and neutral liposome and they found maximum zeta potential obtained at a high pH medium [36]. Finally, zeta potential is not significantly affected by neither HLB value ($X_2$) nor sonication time ($X_4$).

Effect of the Variables on the Entrapment Efficiency

Figure 4A:
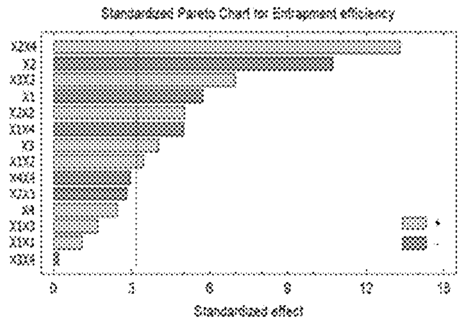
FIGS. 4A-D. Effect of the variables on the entrapment efficiency % of AVA-loaded TRFs; a) standardized Pareto chart; b-d) Response surface plots.

Table 3 revealed that the $X_3$, the interaction terms of $X_1X_2$, and $X_2X_4$, and the quadratic terms of $X_2$ and $X_3$ have significant positive effects on the EE % of AVA in the prepared TRF. While $X_1$ and $X_2$, and the interaction term of $X_1X_4$ showed significant negative effects on $Y_3$. This finding is confirmed by the Pareto chart (FIG. 4*a*). The R-squared was 99.71% and the adjusted R-squared was 98.39%. The model equation was indicated in equation 6.

$$EE\%\ (Y_3)=179.57-0.597X_1-8.101X_2-11.311X_3\pm0.089X_4\pm0.003X_1^2+0.047X_1X_2+0.032X_1X_3-0.002X_1X_4+0.113X_2^2-0.165X_2X_3+0.02X_2X_4+0.727X_3^2-0.0004X_3X_4-0.00008X_4^2 \quad \text{(equation 6)}$$

Figure 4B:
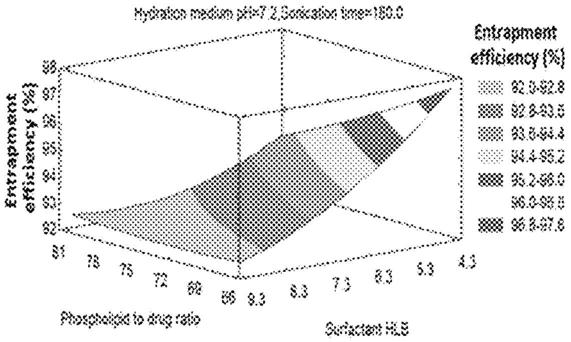
Figure 4C:
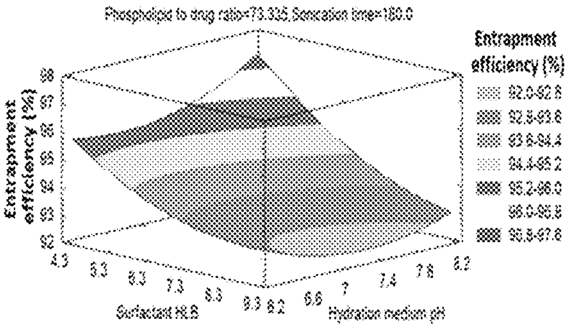
Figure 4D:
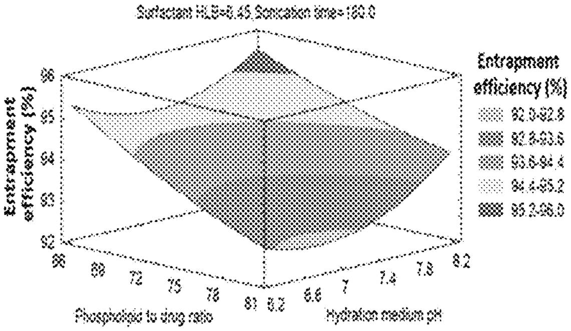
Figure 5A:
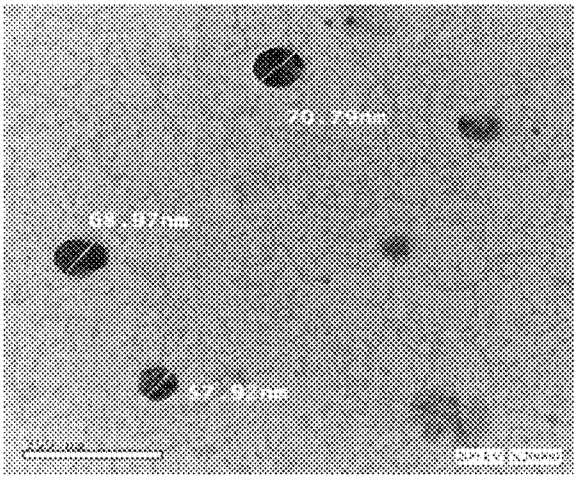
FIGS. 5A-D. Transmission electron microscopic images of a) the optimized AVA TRF, b) plain TRF, c) optimized AVA TRF film, and d) plain TRF film.
Figure 5B:
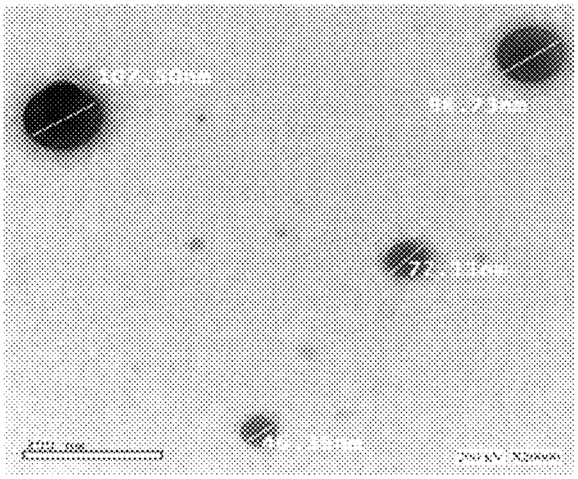
Figure 5C:
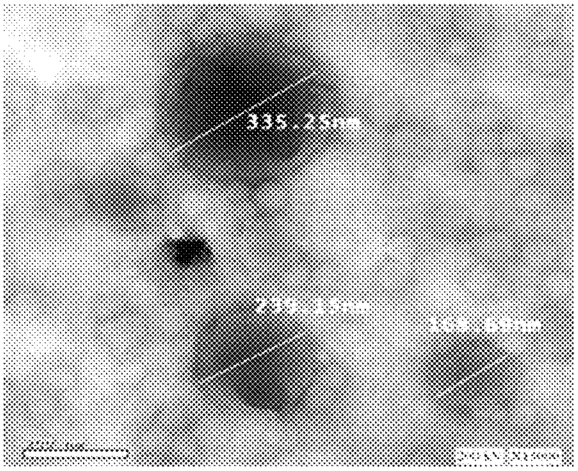
Figure 5D:
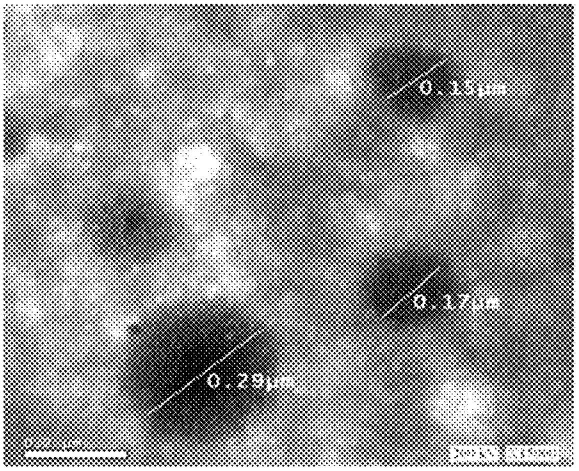
Figure 6A:
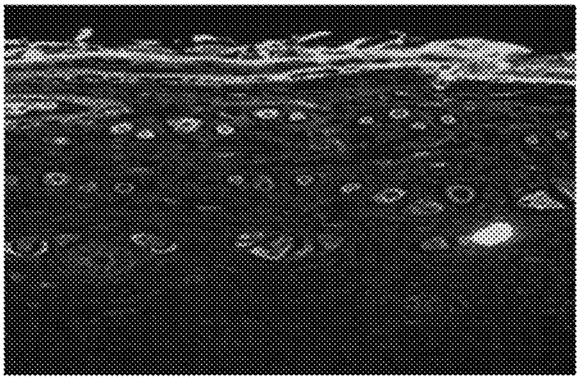
FIGS. 6A-F. Fluorescence laser microscope images for rat skin layers following transdermal application of fluorescence-labeled transfersomal film (Test on the left side) and fluorescence-labeled film (control on the right side) a&b) after 1 h, c&d) after 3 h, and e&f) after 5 h.
Figure 6B:
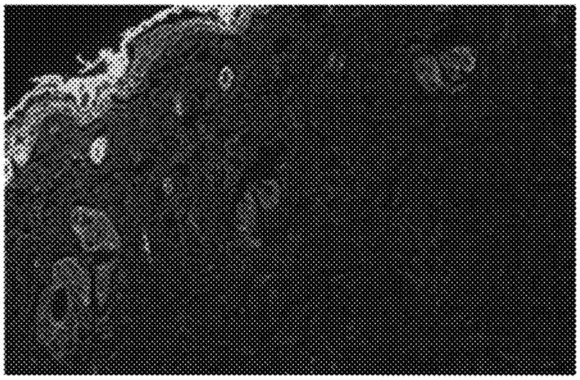
Figure 6C:
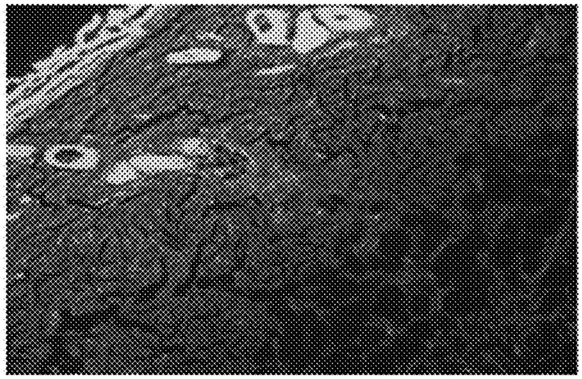
Figure 6D:
Figure 6E:
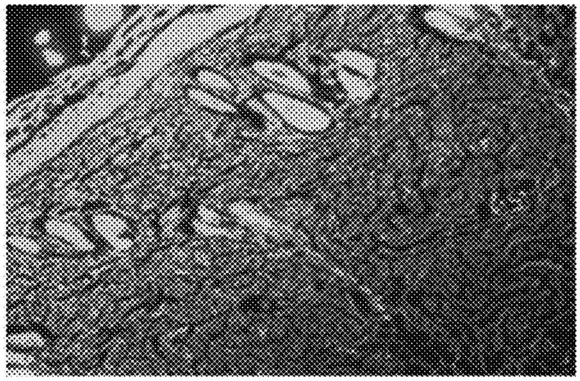
Figure 6F:
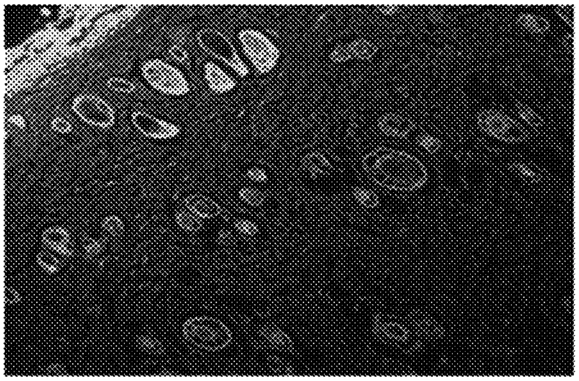

The response surface plots were constructed in FIGS. 4*b*&*d*) to demonstrate the negative effect of phospholipid to drug molar ratio ($X_1$) on $Y_3$. EE % of AVA in TRF decreased with an increased value of $X_1$ from 2:1 to 4:1 as observed in F1, F5, F7, and F10 where its AVA EE % decrease from 97.32, 99.80, 97.18, and 98.43% to 90.52, 92.63, 91.33, and 90.49% in F14, F4, F6, and F13, respectively at the same level of $X_2$ and $X_3$. This finding could be explained by the possible repulsion between the negatively charged AVA and the magnitude of the negativity of TRF due to its content of Phospholipon® 90 G that may facilitate its migration out of vesicles. This decrease in AVA EE % was supported by the same result that was conducted on valsartan as a lipophilic negatively charged drug that shown low EE % in TRF vesicles with increasing the phospholipid ratio [37]. On the other hand, FIGS. 4*b*&*c* demonstrated the negative effect of surfactant HLB value ($X_2$) on $Y_3$. AVA EE % increased with a decrease of surfactant HLB value that was used in TRF preparation. This inverse relationship was observed when the HLB value increase from 2.83 to 10.06, the EE % decrease from 92.63, 99.80, 98.43, and 97.79% in F4, F5, F10, and F15, respectively to 91.33, 97.18, 97.32, and 92.38% in F6, F7, F1, and F2, respectively at the same level of $X_1$ and $X_3$. The decrease in the HLB of surfactants in the formulations leads to an increase in the EE % was supported by previous studies that investigated the role of edge activator and surface charge in developing ultra-deformable vesicles with enhanced skin delivery [27] and the niosomal formulation of Paclitaxel [30]. Besides, there is a direct relationship between the EE % and pH of the hydration medium as illustrated in FIGS. 4*c*&*d*). As the pH of hydration medium increased from 6.2 to 8.2, the EE % of AVA in TRF increases from 98.43, 90.49, and 90.52% in F10, F13, and F14, respectively to 99.8, 92.63, and 91.33% in F5, F4, and F6, respectively at the same level of $X_1$ and $X_2$. Also, increasing the pH of the hydration medium from 5.5 to 8.88 increased the EE % from 95.32 to 96% as in F9 and F11 at equal values of $X_1$ and $X_2$. This is owing to the pH-dependent solubility of AVA making it more soluble in the acidic medium than neutral or alkaline ones [7]. So, when the pH of the hydration medium increased, the solubility of AVA in this medium decreases and thus facilitates its migration into lamellar layers of TRF as shown in a previous study [9]. Finally, it was found that the EE % of AVA in the TRF is not significantly affected by the sonication time ($X_4$).

Multiple Response Optimization for Prediction of the Optimized Formulation

The optimum formulation composition was determined by numerical optimization following a desirability function approach. The optimized formulation with 4.36:1 ($X_1$), 3.36 ($X_2$), 7.8 ($X_3$), and 190s ($X_4$) with a desirability value of 1. This combination revealed 97.75 nm for vesicle size, −28.83 mV for zeta potential, and 95.14% for EE that was very close to the predicted values with a percentage error of 6.90, 2.77, and 1.18%, respectively that affirm the optimization process reliability. The optimized TRF showed a PDI value of 0.282±0.026, indicating a uniform size distribution of vesicles. It worth noting that efficient drug skin penetration from lipid vesicular systems with a size of about 90 nm is more beneficial in drug penetration to deeper skin layers [38].

Deformability of the Optimized AVA-Loaded TRF Formulation

The penetration of lipid vesicles through the skin layers depends on the elasticity of their membrane and therefore the carrier system must be deformed to pass easily over the minutest pores in the skin [39]. The deformability study by the extrusion method was performed on the optimized formulation and the percentage of deformability was 19.42% confirming the elasticity of the vesicles and its capability to penetrate the skin. Morphological examination of TRF using TEM TEM is used as an efficient tool to confirm the results of a vesicle size measurement, as it can create images at high resolution and can also capture any concomitant structures as well as microstructure transitions [40]. FIG. 5 revealed that the formed TRF has a uniform globule size distribution with a nano-size range of approximately 70 nm for optimized AVA TRF dispersion, 80 nm for plain TRF dispersion, 247 nm for optimized AVA TRF film, and 205 nm for plain TRF film and with no aggregation.

Evaluation of the Optimized AVA-Loaded TRF Film

The prepared AVA-loaded TRF films showed uniformity of the drug content of 97.56%±2.93, uniformity of the thickness at different points of 0.35 mm±0.02, and an average elongation percent of 37.5%. These findings reflect the good quality of the prepared films.

Visualization of Skin Permeation of the Optimized AVA-Loaded Transdermal Film Using a Fluorescence Laser Microscope Visualization of the permeation extent of the prepared optimized FITC-dextran-loaded AVA transdermal film was carried out using a fluorescence laser microscope in comparison with raw FITC-dextran-loaded transdermal film. The images revealed marked widespread fluorescence intensity in skin tissue from FITC-dextran-loaded AVA TRF film after 1, 3, and 5 h compared to raw FITC-dextran-loaded transdermal formulation as shown in FIG. 6. The images revealed permeation enhancement from FITC-dextran-loaded AVA TRF film through different skin layers. This result could be attributed to the deformability of the TRF structure that enhances its penetration through skin layers compared with the film containing raw AVA.

In Vivo Pharmacokinetic Parameters

Figure 7:
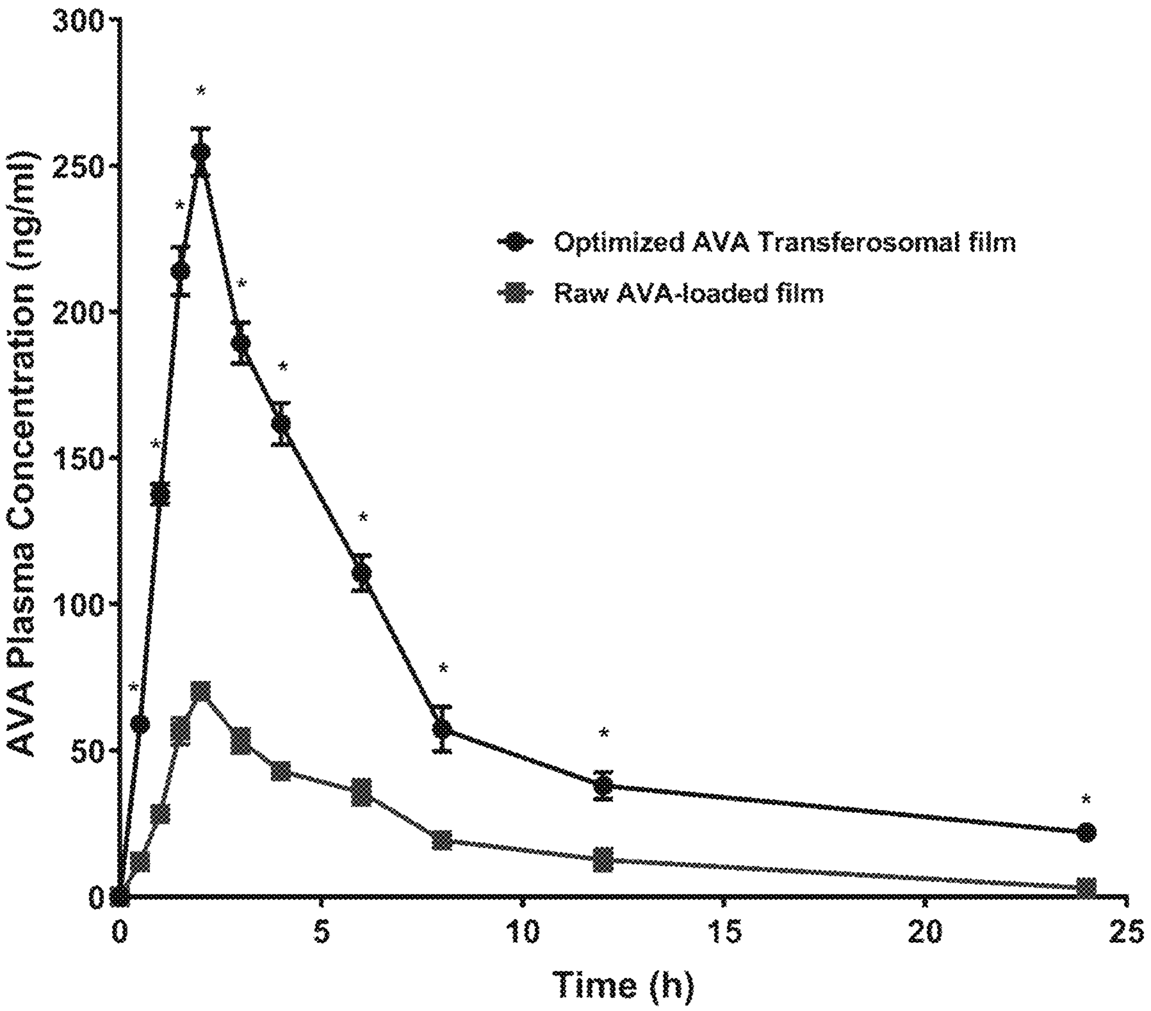
FIG. 7. AVA plasma concentration-time curve following transdermal application of optimized AVA-loaded TRF films compared to raw AVA-loaded films.

The mean concentrations of AVA in rats' plasma following transdermal application of a single dose (20 mg/kg) from the optimized AVA-loaded TRF films and raw AVA-loaded films are graphically illustrated in FIG. 7. The optimized AVA-loaded TRF film demonstrated significantly higher maximum plasma concentration ($C_{max}$) and AUC ($P<0.05$) relative to the raw AVA-loaded film as shown in Table 4. The C. of the optimized AVA-loaded TRF film was 254.66±8.02 ng/ml, compared to 70.33±3.05 ng/ml of the raw AVA-loaded film. Also, optimized AVA-loaded TRF film showed an area under the curve of 2050.45±159.14 ng/ml h in comparison to the raw AVA film 497.34±102.61 ng/ml h. The relative bioavailability of AVA-loaded TRF film was 412.28% compared to raw AVA film and both films reached maximum plasma concentrations after a median time of 2 h. This enhancement of the bioavailability could lead n reducing drug dose and thus will reduce its related side effects. The increased absorption extent of the drug following transdermal application of the optimized AVA-loaded TRF film could be credited to the enhanced permeation of the drug resulting from squeezing and deformability of ultra-deformable vesicles as previously confirmed by visualization of skin permeation using a fluorescence laser microscope. Furthermore, the nano size of the vesicles contributes to the permeation effect, since the small vesicles provide a large surface area that makes the contact of the vesicles with the skin membrane higher thus increasing the skin permeation [9]. These results highlight the effeectiveness of TRF to enhance AVA transdermal delivery.

TABLE 4

Pharmacokinetic parameters following the transdermal application of the optimized AVA-loaded TRF films and raw AVA-loaded films.

| PK parameters | AVA-loaded TRF Film | Raw AVA-loaded Film |
|---|---|---|
| Lambda_z (1/h) | 0.05659 ± 0.0055 | 0.129 ± 0.06 |
| t1/2 (h) | 12.32 ± 1.20 | 6.09 ± 2.46 |
| $T_{max}$ (h) | 2 | 2 |
| $C_{max}$ (ng/ml) | 254.66 ± 8.02 | 70.33 ± 3.05 |
| AUC 0-t (ng/ml * h) | 1657.5 ± 100.55 | 449.75 ± 102.23 |
| AUC 0-inf (ng/ml * h) | 2050.45 ± 159.14 | 497.34 ± 102.61 |
| AUMC 0-inf (ng/ml * h^2) | 28180.98 ± 4850.72 | 4301.72 ± 1759.154 |
| MRT 0-inf (h) | 13.69 ± 1.45 | 8.38 ± 2.12 |
| Vz/F (mg/kg)/(ng/ml) | 0.17 ± 0.017 | 0.34 ± 0.08 |
| Cl/F (mg/kg)/(ng/ml)/h | 0.0097 ± 0.00077 | 0.041 ± 0.0097 |

Significant difference at $p<0.05$ (unpaired t-test with Welch's correction). AUC, the area under the time-concentration curve; $C_{max}$, maximum plasma concentration; $T_{max}$, the time required to reach the $C_{max}$; Lambda_z, elimination rate constant; MRT, the mean residence time; Vz, Apparent volume of distribution during terminal phase; Cl/F, apparent total clearance of the drug from plasma after drug oral administration.

CONCLUSION

From the obtained results, it can be concluded that the Draper-Lin small composite design succeeded to explore the effect of the independent variables on the quality of AVA-loaded TRF. The design optimized these variables to prepare AVA-loaded TRF with minimum vesicle size, maximum zeta potential, and maximum entrapment efficiency. The deformability and in vitro release of AVA from the prepared TRF showed good deformability and release profiles. On incorporation of the optimized formulation in transdermal films, the prepared films showed uniformity in their thickness and drug content as well as good elasticity. Also, the visualization of the permeation efficiency of the vesicles from the transdermal film through the rat skin displayed an intense discoloration in the deep skin layer in comparison with raw AVA-loaded films using a fluorescence laser microscope. Finally, the pharmacokinetic parameters indicated that the increased absorption extent of the drug following transdermal application of the optimized AVA-loaded TRF film.

REFERENCES

1. Jumani, D. K. New Approach to Management of Erectile Dysfunction in 2017. *In beyond medicine;* 2017; Vol. 3, pp. 1044-1050.
2. Hackett, G.; Kirby, M.; Wylie, K.; Heald, A.; Ossei-Gerning, N.; Edwards, D.; Muneer, A. British Society for Sexual Medicine Guidelines on the Management of Erectile Dysfunction in Men-2017. *J. Sex. Med.* 2018, 15, 430-457, doi:10.1016/j.jsxm.2018.01.023.
3. El-Sakka, A. I. Erectile dysfunction in Arab countries. Part I: Prevalence and correlates. *Arab J. Urol.* 2012, 10, 97-103, doi:10.1016/j.aju.2012.01.004.

4. Fahmy, U. A. Nanoethosomal transdermal delivery of vardenafil for treatment of erectile dysfunction: Optimization, characterization, and in vivo evaluation. *Drug Des. Devel. Ther.* 2015, 9, 6129-6137, doi:10.2147/DDDT.S94615.
5. Corona, G.; Maggi, M.; Jannini, E. Avanafil: The Second-Generation Treatment of Erectile Dysfunction. *Eur. Med. J.* 2016, 61-69.
6. Saxena, A.; Parakash, P.; Porwal, M.; Sissodia, N.; Sharma, P. Erectile dysfunction: A review and herbs used for its treatment. *Int. J. Green Pharm.* 2012, 6, 109-117, doi:10.4103/0973-8258.102825.
7. Burke, R. M.; Evans, J. D. Avanafil for treatment of erectile dysfunction: Review of its potential. *Vasc. Health Risk Manag.* 2012, 8, 517-523, doi:10.2147/VHRM.S26712.
8. Patel, A.; Nair, A.; Prajapati, P.; Jadhav, A. Formulation and Evaluation of Avanafil Orodispersible Tablet. *Int. J. Chem. Pharm. Sci.* 2015, 3, 1975-1986.
9. Hosny, K. M.; Ahmed, O. A. A.; Fahmy, U. A.; Alkhalidi, H. M. Nanovesicular systems loaded with a recently approved second generation type-5 phospodiesterase inhibitor (avanafil): I. Plackett-Burman screening and characterization. *J. Drug Deliv. Sci. Technol.* 2018, 43, 154-159, doi:10.1016/j.jddst.2017.10.009.
10. Shrestha, H.; Bala, R.; Arora, S. Lipid-Based Drug Delivery Systems. *J. Pharm.* 2014, 2014, 10.
11. Cevc, G.; Blume, G. Lipid vesicles penetrate into intact skin owing to the transdermal osmotic gradients and hydration force. *BBA—Biomembr.* 1992, 1104, 226-232, doi:10.1016/0005-2736(92)90154-E.
12. Ahmed, T. A. Preparation of TRFs encapsulating sildenafil aimed for transdermal drug delivery: Plackett-Burman design and characterization. *J. Liposome Res.* 2015, 25, 1-10, doi:10.3109/08982104.2014.950276.
13. Pawar, A. Y.; Jadhav, K. R.; Chaudhari, L. H. TRF: A Novel Technique Which Improves Transdermal Permeability. *Asian J. Pharm.* 2016, 10, 425-436.
14. Kumar, A.; Pathak, K.; Bali, V. Ultra-adaptable nanovesicular systems: a carrier for systemic delivery of therapeutic agents. *Drug Discov. Today* 2012, 17, 1233-41, doi:10.1016/j.drudis.2012.06.013.
15. Pradhan, M.; Singh, D.; Singh, M. R. Novel colloidal carriers for psoriasis: current issues, mechanistic insight and novel delivery approaches. *J. Control. release* 2013, 170, 380-95, doi:10.1016/j.jconrel.2013.05.020.
16. Sarmah, P. J.; Kalita, B.; Sharma, A. K. TRFS BASED TRANSDERMAL DRUG DELIVERY: AN OVERVIEW. *Int. J. Adv. Pharm. Res.* 2013, 4, 2555-2563.
17. Sciences, M.; Sarkar, B. K.; Maharshi, A.; Baniwal, A.; Kumar, S.; Road, B.; Gaon, M.; Nagar, R. Formulation and Characterization of Quercetin TRF for Transdermal Delivery. *Int. J. Pharm. Med. Sci.* 2012, 1, 28-38.
18. Al Shuwaili, A. H.; Rasool, B. K. A.; Abdulrasool, A. A. Optimization of elastic TRFs formulations for transdermal delivery of pentoxifylline. *Eur. J. Pharm. Biopharm.* 2016, 102, 101-114, doi:10.1016/j.ejpb.2016.02.013.
19. Patel, R.; Singh, S. K.; Singh, S.; Sheth, N. R.; Gendle, R. Development and characterization of curcumin loaded TRF for transdermal delivery. *J. Pharm. Sci. Res.* 2009, 1, 71-80.
20. El-Say, K. M.; Hosny, K. M. Optimization of carvedilol solid lipid nanoparticles: An approach to control the release and enhance the oral bioavailability on rabbits. *PLoS One* 2018, 13, e0203405, doi:10.1371/JOURNAL.PONE.0203405.
21. Fahmy UA, A. B. Stability indicating HPLC method for analysis of avanafil using diode array detector. *Int. J. Adv. Pharm. Biol. Chem.* 2016, 5, 59-64.
22. Ahmed, T. A.; El-Say, K. M.; Aljaeid, B. M.; Fahmy, U. A.; Abd-Allah, F. I. Transdermal glimepiride delivery system based on optimized ethosomal nano-vesicles: Preparation, characterization, in vitro, ex vivo and clinical evaluation. *Int. Journal Pharm.* 2016, 500, 245-254, doi:10.1016/j.ijpharm.2016.01.017.
23. El-Say, K. M.; Ahmed, T. A.; Badr-Eldin, S. M.; Fahmy, U.; Aldawsari, H.; Ahmed, O. A. A Enhanced permeation parameters of optimized nanostructured simvastatin transdermal films: ex vivo and in vivo evaluation. *Pharm. Dev. Technol.* 2015, 20, 919-926, doi:10.3109/10837450.2014.938859.
24. Ahmed, T. A.; El-Say, K. M. Development of alginate-reinforced chitosan nanoparticles utilizing W/O nanoemulsification/internal crosslinking technique for transdermal delivery of rabeprazole. *Life Sci.* 2014, 110, 35-43, doi:10.1016/j.lfs.2014.06.019.
25. Ahmed, O. A. A.; El-Say, K. M.; Aljaeid, B. M.; Badr-Eldin, S. M.; Ahmed, T. A. Optimized vinpocetine-loaded vitamin E D-a-tocopherol polyethylene glycol 1000 succinate-alpha lipoic acid micelles as a potential transdermal drug delivery system: in vitro and ex vivo studies. *Int. J. Nanomedicine* 2018, Volume 14, 33-43, doi:10.2147/LIN.S187470.
26. Thavarajah, R.; Mudimbaimannar, V. K.; Elizabeth, J.; Rao, U. K.; Ranganathan, K. Chemical and physical basics of routine formaldehyde fixation. *J. Oral Maxillofac. Pathol.* 2012, 16, 400-405.
27. El Zaafarany, G. M.; Awad, G. A. S.; Holayel, S. M.; Mortada, N. D. Role of edge activators and surface charge in developing ultradeformable vesicles with enhanced skin delivery. *Int. J. Pharm.* 2010, 397, 164-72, doi:10.1016/j.ijpharm.2010.06.034.
28. El-Laithy, H. M.; Shoukry, O.; Mahran, L. G. Novel sugar esters proniosomes for transdermal delivery of vinpocetine: preclinical and clinical studies. *Eur. J. Pharm. Biopharm.* 2011, 77, 43-55, doi:10.1016/j.ejpb.2010.10.011.
29. Nasr, M.; Mansour, S.; Mortada, N. D.; Elshamy, A. A. Vesicular aceclofenac systems: A comparative study between liposomes and niosomes. *J. Microencapsul.* 2008, 25, 499-512, doi:10.1080/02652040802055411.
30. Bayindir, Z. S.; Yuksel, N. Characterization of niosomes prepared with various nonionic surfactants for paclitaxel oral delivery. *J. Pharm. Sci.* 2010, 99, 2049-2060, doi:10.1002/jps.21944.
31. Johnston, M. J. W.; Semple, S. C.; Klimuk, S. K.; Edwards, K.; Eisenhardt, M. L.; Leng, E. C.; Karlsson, G.; Yanko, D.; Cullis, P. R. Therapeutically optimized rates of drug release can be achieved by varying the drug-to-lipid ratio in liposomal vincristine formulations. *Biochim. Biophys. Acta* 2006, 1758, 55-64, doi:10.1016/j.bbamem.2006.01.009.
32. El-Say, K. M.; El-Helw, A.; Ahmed, O. A. A.; Hosny, M.; Ahmed, T. A.; Kharshoum, R. M.; Fahmy, U. A.; Al-Sawahli, M. M. Statistical optimization of controlled release microspheres containing cetirizine hydrochloride as a model for water soluble drugs. *Pharm. Dev. Technol.* 2015, 20, doi:10.3109/10837450.2014.920353.
33. Jamal, M.; Imam, S S; Aqil, M.; Amir, M.; Mir, S. R.; Mujeeb, M. Transdermal potential and anti-arthritic efficacy of ursolic acid from niosomal gel systems. *Int. Immunopharmacol.* 2015, 29, 361-369, doi:10.1016/j.intimp.2015.10.029.

34. Pardakhty, A.; Varshosaz, J.; Rouholamini, A. In vitro study of polyoxyethylene alkyl ether niosomes for delivery of insulin. *Int. J. Pharm.* 2007, 328, 130-41, doi: 10.1016/j.ijpharm.2006.08.002.

35. Das, S.; Ng, W. K.; Tan, R. B. H. Are nanostructured lipid carriers (NLCs) better than solid lipid nanoparticles (SLNs): Development, characterizations and comparative evaluations of clotrimazole-loaded SLNs and NLCs? *Eur. J. Pharm. Sci.* 2012, 47, 139-151, doi:10.1016/j.ejps.2012.05.010.

36. Smith, M. C.; Crist, R. M.; Clogston, J. D.; McNeil, S. E. Zeta potential: a case study of cationic, anionic, and neutral liposomes. *Anal. Bioanal. Chem.* 2017, 409, 5779-5787, doi:10.1007/s00216-017-0527-z.

37. Ahad, A.; Aqil, M.; Kohli, K.; Sultana, Y.; Mujeeb, M.; Ali, A. Formulation and optimization of nanoTRFs using experimental design technique for accentuated transdermal delivery of valsartan. *Nanomedicine Nanotechnology, Biol. Med.* 2012, 8, 237-249, doi:10.1016/j.nano.2011.06.004.

38. Lin, H. W.; Xie, Q. C.; Huang, X.; Ban, J. F.; Wang, B.; Wei, X.; Chen, Y. Z.; Lu, Z. F. Increased skin permeation efficiency of imperatorin via charged ultradeformable lipid vesicles for transdermal delivery. *Int. J. Nanomedicine* 2018, 13, 831-842, doi:10.2147/LIN.S150086.

39. Song, C. K.; Balakrishnan, P.; Shim, C.-K.; Chung, S.-J.; Chong, S.; Kim, D.-D. A novel vesicular carrier, transethosome, for enhanced skin delivery of voriconazole: Characterization and in vitro/in vivo evaluation. *Colloids Surfaces B Biointerfaces* 2012, 92, 299-304, doi:10.1016/j.colsurfb.2011.12.004.

40. Dave, V.; Yadav, R. B.; Ahuja, R.; Yadav, S. Formulation design and optimization of novel fast dissolving tablet of chlorpheniramine maleate by using lyophilization techniques. *Bull. Fac. Pharmacy, Cairo Univ.* 2017, 55, 31-39, doi:10.1016/j.bfopcu.2016.12.001.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A transdermal film formulation, comprising transfersomes incorporated onto the transdermal film, wherein the transfersomes comprise:

avanafil;

a phospholipid; and an edge activator, wherein the phospholipid to avanafil ratio is from 3.5:1 to 4.5:1, wherein the edge activator is a surfactant having a hydrophilic-lipophilic (HLB) value of 2-4, wherein the phospholipid to edge activator ratio is from 2.5:1 to 3.5:1, and wherein the formulation does not include ethanol.

2. The transdermal film formulation of claim 1, wherein the phospholipid is phosphatidylcholine stabilized with ascorbyl palmitate.

3. The transdermal film formulation of claim 1, wherein the film further comprises hydroxypropyl methylcellulose (HPMC), citral, and propylene glycol.

4. The transdermal film formulation of claim 3, wherein the HPMC is present in an amount of 1-5% w/v.

5. The transdermal film formulation of claim 3, wherein the citral is present in an amount of 1-5% w/v.

6. The transdermal film formulation of claim 3, wherein the propylene glycol is present in an amount of 1-5% w/v.

7. A method of making the transdermal film formulation of claim 1, comprising:

preparing the transfersomes comprising the avanafil, the phospholipid and the edge activator, wherein the phospholipid to avanafil ratio is from 3.5:1 to 4.5:1, wherein the edge activator is a surfactant having a hydrophilic-lipophilic (HLB) value of 2-4, wherein the phospholipid to edge activator ratio is from 2.5:1 to 3.5:1, and wherein the transfersomes are present in a hydration medium at a pH of 7.5-8.5;

mixing the transfersomes with a film-forming polymer, a penetration enhancer, and a plasticizer to produce a gel; and drying the gel to produce a film.

8. The method of claim 7, wherein the film-forming polymer is HPMC, the penetration enhancer is citral, and the plasticizer is propylene glycol.

9. The method of claim 8, wherein the HPMC is added in an amount of 1-5% w/v.

10. The method of claim 8, wherein the citral is added in an amount of 1-5% w/v.

11. The method of claim 8, wherein the propylene glycol is added in an amount of 1-5% w/v.

12. A method of delivering avanafil to a subject in need thereof, comprising applying the transdermal film formulation of claim 1 to the skin of the subject.

* * * * *